United States Patent
Seidling et al.

(10) Patent No.: US 9,545,365 B2
(45) Date of Patent: Jan. 17, 2017

(54) TEMPERATURE CHANGE COMPOSITIONS AND TISSUE PRODUCTS PROVIDING A COOLING SENSATION

(71) Applicant: Kimberly-Clark Worldwide, Inc., Neenah, WI (US)

(72) Inventors: Jeffery Richard Seidling, Appleton, WI (US); Helen Kathleen Moen, Hortonville, WI (US); Scott W. Wenzel, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 3 days.

(21) Appl. No.: 14/877,187

(22) Filed: Oct. 7, 2015

(65) Prior Publication Data
US 2016/0022553 A1    Jan. 28, 2016

Related U.S. Application Data

(62) Division of application No. 12/622,547, filed on Nov. 20, 2009, now Pat. No. 9,181,465.

(51) Int. Cl.
*A61K 8/02* (2006.01)
*A61K 8/06* (2006.01)
(Continued)

(52) U.S. Cl.
CPC ............... *A61K 8/06* (2013.01); *A61K 8/0208* (2013.01); *A61K 8/34* (2013.01); *A61K 8/345* (2013.01);
(Continued)

(58) Field of Classification Search
CPC ......... A61K 8/0208; A61K 8/06; A61Q 19/00
See application file for complete search history.

(56) References Cited

U.S. PATENT DOCUMENTS

| 1,253,603 A | 1/1918 | Keagy |
| 1,579,124 A | 3/1926 | Faulder |

(Continued)

FOREIGN PATENT DOCUMENTS

| BE | 0 905 997 A | 4/1987 |
| DE | 10313101 A1 | 7/2004 |

(Continued)

OTHER PUBLICATIONS

Otto et al., "Formulation effects of topical emulsions on transdermal and dermal delivery", published online Jan. 6, 2009, International Journal of Cosmetic Science, vol. 31, pp. 1-19.*

(Continued)

*Primary Examiner* — Michael B Pallay
(74) *Attorney, Agent, or Firm* — Kimberly-Clark Worldwide, Inc.

(57) ABSTRACT

Wiping products, such as facial tissues, contain a temperature change composition that can provide a cooling sensation when contacted with the skin of a user. The temperature change composition is structured emulsion that may include a phase change material, a carrier, a surfactant, and a crystalline initiator. The phase change materials, in one embodiment, can have a relatively high heat of fusion. When undergoing a phase change, the temperature change composition absorbs heat and thereby provides a cooling feeling or cooling sensation to the skin of a user.

8 Claims, 3 Drawing Sheets

(51) Int. Cl.

| | | |
|---|---|---|
| A61Q 19/00 | (2006.01) | |
| A61K 8/34 | (2006.01) | |
| A61K 8/37 | (2006.01) | |
| A61K 8/60 | (2006.01) | |
| A61K 8/92 | (2006.01) | |
| C09K 5/06 | (2006.01) | |
| D21H 27/00 | (2006.01) | |
| D21H 21/14 | (2006.01) | |
| D21H 27/30 | (2006.01) | |

(52) U.S. Cl.
CPC . *A61K 8/37* (2013.01); *A61K 8/60* (2013.01); *A61K 8/92* (2013.01); *A61Q 19/00* (2013.01); *C09K 5/063* (2013.01); *D21H 27/002* (2013.01); *A61K 2800/244* (2013.01); *D21H 21/14* (2013.01); *D21H 27/30* (2013.01)

(56) References Cited

U.S. PATENT DOCUMENTS

| | | |
|---|---|---|
| 1,885,278 A | 11/1932 | Monett |
| 2,721,554 A | 10/1955 | George |
| 3,264,172 A | 8/1966 | Regutti |
| 3,301,746 A | 1/1967 | Sanford et al. |
| 3,516,941 A | 6/1970 | Matson |
| 3,585,104 A | 6/1971 | Kleinert |
| 3,607,348 A | 9/1971 | Wray et al. |
| 3,812,000 A | 5/1974 | Salvucci et al. |
| 3,974,025 A | 8/1976 | Ayers |
| 4,100,324 A | 7/1978 | Anderson et al. |
| 4,191,609 A | 3/1980 | Trokhan |
| 4,208,459 A | 6/1980 | Becker et al. |
| 4,504,442 A | 3/1985 | Rosenblatt et al. |
| 4,514,345 A | 4/1985 | Johnson et al. |
| 4,528,239 A | 7/1985 | Trokhan |
| 4,585,482 A | 4/1986 | Tice et al. |
| 4,594,130 A | 6/1986 | Chang et al. |
| 4,604,313 A | 8/1986 | McFarland et al. |
| 4,637,859 A | 1/1987 | Trokhan |
| 4,793,898 A | 12/1988 | Laamanen et al. |
| 4,985,064 A | 1/1991 | Redlich et al. |
| 5,098,522 A | 3/1992 | Smurkoski et al. |
| 5,126,070 A | 6/1992 | Leifheit et al. |
| 5,275,700 A | 1/1994 | Trokhan |
| 5,328,565 A | 7/1994 | Rasch et al. |
| 5,350,624 A | 9/1994 | Georger et al. |
| 5,496,624 A | 3/1996 | Stelljes, Jr. et al. |
| 5,529,665 A | 6/1996 | Kaun |
| 5,554,467 A | 9/1996 | Trokhan et al. |
| 5,566,724 A | 10/1996 | Trokhan et al. |
| 5,595,627 A | 1/1997 | Gordon et al. |
| 5,628,876 A | 5/1997 | Ayers et al. |
| 5,693,255 A | 12/1997 | Okamoto et al. |
| 5,840,671 A | 11/1998 | Fujimura et al. |
| 6,028,018 A | 2/2000 | Amundson et al. |
| 6,187,695 B1 | 2/2001 | Krzysik et al. |
| 6,258,249 B1 | 7/2001 | Simpson |
| 6,338,855 B1 | 1/2002 | Albacarys et al. |
| 6,428,794 B1 | 8/2002 | Klofta et al. |
| 6,432,270 B1 | 8/2002 | Liu et al. |
| 6,582,558 B1 | 6/2003 | Liu |
| 6,749,860 B2 | 6/2004 | Tyrrell et al. |
| 6,825,393 B2 | 11/2004 | Roe et al. |
| 6,855,410 B2 | 2/2005 | Buckley |
| 6,860,967 B2 | 3/2005 | Baumoller et al. |
| 6,896,766 B2 | 5/2005 | Sarbo et al. |
| 6,949,167 B2 | 9/2005 | Shannon et al. |
| 7,005,557 B2 | 2/2006 | Klofta et al. |
| 7,008,507 B2 | 3/2006 | Urlaub et al. |
| 7,300,547 B2 | 11/2007 | Luu et al. |
| 7,361,361 B2 | 4/2008 | Luu et al. |
| 7,485,373 B2 | 2/2009 | Krzysik et al. |
| 7,582,577 B2 | 9/2009 | Vinson |
| 8,480,852 B2 * | 7/2013 | Wenzel ............... A61K 8/0208 162/124 |
| 8,795,717 B2 * | 8/2014 | Moen ..................... A47K 10/16 252/71 |
| 2002/0051823 A1 | 5/2002 | Yan et al. |
| 2002/0192552 A1 | 12/2002 | Lampe-Onnerud et al. |
| 2003/0077962 A1 | 4/2003 | Krzysik et al. |
| 2003/0095990 A1 | 5/2003 | Hua et al. |
| 2003/0108761 A1 | 6/2003 | Eddlemon |
| 2003/0133832 A1 | 7/2003 | D Ottone |
| 2003/0147773 A1 | 8/2003 | Bryner et al. |
| 2003/0174810 A1 | 9/2003 | Korenev et al. |
| 2003/0188841 A1 | 10/2003 | Buder et al. |
| 2003/0230492 A1 | 12/2003 | Kadlec et al. |
| 2004/0009223 A1 | 1/2004 | Garg et al. |
| 2004/0076544 A1 | 4/2004 | Dao |
| 2004/0140347 A1 | 7/2004 | Mihaylov et al. |
| 2004/0186085 A1 * | 9/2004 | Simonnet ............... A61K 8/345 514/178 |
| 2004/0234561 A1 | 11/2004 | Ansmann et al. |
| 2005/0058674 A1 | 3/2005 | Joseph et al. |
| 2005/0058693 A1 | 3/2005 | Joseph et al. |
| 2005/0136765 A1 | 6/2005 | Shannon |
| 2005/0238701 A1 | 10/2005 | Kleinwaechter |
| 2005/0250402 A1 | 11/2005 | Wild et al. |
| 2005/0274470 A1 | 12/2005 | Shannon et al. |
| 2006/0147502 A1 | 7/2006 | Koenig et al. |
| 2006/0233986 A1 | 10/2006 | Gutsche et al. |
| 2007/0148446 A1 | 6/2007 | Brown et al. |
| 2007/0148447 A1 | 6/2007 | Amundson et al. |
| 2007/0148448 A1 | 6/2007 | Joseph et al. |
| 2007/0202185 A1 | 8/2007 | Amundson et al. |
| 2008/0045913 A1 | 2/2008 | Johnson et al. |
| 2008/0188560 A1 | 8/2008 | Mohammadi et al. |
| 2009/0110656 A1 | 4/2009 | Lemke et al. |
| 2009/0155325 A1 | 6/2009 | Magin et al. |
| 2009/0297586 A1 | 12/2009 | Shannon et al. |
| 2011/0123578 A1 | 5/2011 | Wenzel et al. |
| 2011/0124769 A1 | 5/2011 | Moen et al. |

FOREIGN PATENT DOCUMENTS

| | | |
|---|---|---|
| EP | 0 217 105 A | 4/1987 |
| EP | 1 078 980 A1 | 2/2001 |
| EP | 1360954 A2 | 11/2003 |
| EP | 2127737 A2 | 12/2009 |
| GB | 0 004 796 A | 7/1914 |
| GB | 0 016 501 A | 8/1916 |
| GB | 0 107 922 A | 7/1917 |
| JP | 63-296758 A | 12/1988 |
| JP | 09-276027 A | 10/1997 |
| JP | 2000-163629 A | 6/2000 |
| JP | 2001-043447 A | 2/2001 |
| JP | 2001-192306 A | 7/2001 |
| JP | 2005-187723 A | 7/2005 |
| JP | 2005-241285 A | 9/2005 |
| WO | WO 99/42658 A1 | 8/1999 |
| WO | WO 00/66835 A1 | 11/2000 |
| WO | WO 03/035238 A2 | 5/2003 |

OTHER PUBLICATIONS

Avato, P. et al., "Allylsulfide Constituents of Garlic Volatile Oil as Antimicrobial Agents," Phytomedicine, vol. 7, No. 3, 2000, pp. 239-243.

Baysan, A. et al., "Antimicrobial Effect of a Novel Ozone-Generating Device on Micro-Organisms Associated With Primary Root Carious Lesions In Vitro," Journal of the European Organisation for Caries Research (ORCA), vol. 34, No. 6, Nov.-Dec. 2000, pp. 498-501.

Cosentino, S. et al., "In-Vitro Antimicrobial Activity and Chemical Composition of Sardinian Thymus Essential Oils," Letters in Applied Microbiology, vol. 29(2), 1999, pp. 130-135.

Demirci, Fatih et al., "Antimicrobial Activities of Ferulago Essential Oils," Zeitschrift fur Naturforschung C, vol. 55, No. 11-12, Nov.-Dec. 2000, pp. 886-889.

Djupesland, Per G. et al., "Nitric Oxide in the Nasal Airway: A New Dimension in Otorhinolaryngology," American Journal of Otolar- (56) References Cited

OTHER PUBLICATIONS yngology—Head and Neck Medicine and Surgery, vol. 22, No. 1, Jan.-Feb. 2001, pp. 19-32.
Ender, Peter, "Contaminated Currency: The True Return on the Dollar," Wright-Patterson AFB Medical Center, 101st General Meeting of the American Society for Microbiology, Orlando, FL, May 20-24, 2001, Session 220/C, Paper C-332.
Flamini, Guido et al., "Antimicrobial Activity of the Essential Oil of Calamintha nepeta and its Constituent Pulegone Against Bacteria and Fungi," Phytotherapy Research, vol. 13, No. 4, 1999, pp. 349-351.
Inoue, T. et al., "Solid-Liquid Phase Behavior of Binary Fatty Acid Mixtures 3. Mixtures of Oleic Acid With Capric Acid (Decanoic Acid) and Caprylic Acid (Octanoic Acid)," Chemistry and Physics of Lipids, vol. 132, 2004, pp. 225-234.
Karatzas A.K. et al., "The Combined Action of Carvacrol and High Hydrostatic Pressure on Listeria monocytogenes Scott A," Journal of Applied Microbiology, vol. 90, No. 3, 2001, pp. 463-469.
Kulevanova, S. et al., "Investigation of Antimicrobial Activity of Essential Oils of Several *Macedonian thymus* L. Species (Lamiaceae)," Bollettino Chimico Farmaceutico, vol. 139, No. 6, Nov.-Dec. 2000, pp. 276-280.
Liu, Wai-Kin et al., "Mechanisms of the Bactericidal Activity of Low Amperage Electric Current (DC)," Journal of Antimicrobial Chemotherapy, vol. 39, No. 6, 1997, pp. 687-695.
Marcinkiewicz, Janusz, "Nitric Oxide and Antimicrobial Activity of Reactive Oxygen Intermediates," Immunopharmacology, vol. 37, No. 1, Aug. 1997, pp. 35-41.
Messick, Chad R. et al., "In-Vitro Activity of Polyhexamethylene Biguanide (PHMB) Against Fungal Isolates Associated With Infective Keratitis," The Journal of Antimicrobial Chemotherapy, vol. 44, 1999, pp. 297-298.
Ruberto, Giuseppe et al., "Antioxidant and Antimicrobial Activity of Foeniculum vulgare and Crithmum maritimum, Essential Oils," Planta Medica, vol. 66, No. 8, Dec. 2000, pp. 687-693.
Smith, Anthony W. et al., "Nitric Oxide-Induced Potentiation of the Killing of Burkholderia cepacia by Reactive Oxygen Species: Implications for Cystic Fibrosis," The Journal of Medical Microbiology, vol. 48, No. 5, May 1999, DD. 419-423.
Tappi Official Test Method T 411 om-89, "Thickness (Caliper) of Paper, Paperboard, and Combined Board," published by the TAPPI Press, Atlanta, Georgia, revised 1989, pp. 1-3.
Wang, Hai-Hong et al., "Inhibition of *Escherichia coli* by Dimethyl Fumarate," International Journal of Food Microbiology, vol. 65, Nos. 1-2, 2001, pp. 125-130.
Webert, Kathryn E. et al., "Effects of Inhaled Nitric Oxide in a Rat Model of Pseudomonas aeruginosa Pneumonia," Critical Care Medicine, vol. 28, No. 7, Jul. 2000, pp. 2397-2405.
Flick, Ernest W., "Cosmetics Additives: An Industrial Guide," Noyes Publications, 1991, p. 178.

\* cited by examiner

TEMPERATURE CHANGE COMPOSITIONS AND TISSUE PRODUCTS PROVIDING A COOLING SENSATION

RELATED APPLICATIONS

The present application is a divisional application and claims priority to U.S. patent application Ser. No. 12/622,547, filed on Nov. 20, 2009, which is incorporated herein by reference.

BACKGROUND

Numerous healthcare and cosmetic products are applied to the skin in order to provide various benefits. Such products can include, for instance, lotions, creams, moisturizers, and the like. In some circumstances, the products are intended to provide a cooling feeling or cooling sensation to the skin once applied. Existing products typically provide skin cooling by combining skin cooling agents with other substances.

There are several different means to impart a cooling sensation to the skin, including using evaporation, neurosensory components, or thermodynamic agents such as phase change materials. One example of a cooling agent is menthol which provides cooling in the form of a physiological or neurosensory effect on nerve endings in the human body that sense temperature. The cooling sensation from menthol is not due to latent heat of evaporation but appears to be the result of direct stimulus on the cold receptors at the nerve endings.

The use of phase change materials to impart cooling is discussed, for instance, in PCT International Publication No. WO 2006/007564 entitled "Cosmetic Compositions and Methods for Sensory Cooling", which is incorporated herein by reference. In the '564 application, a skincare cosmetic composition is described in the form of a lotion that is intended for use in after-sun products, after-shave products, and body moisturizing products. The lotion is intended to create a cooling sensation on the skin by incorporating into the lotion components that absorb heat from the skin. In particular, ingredients are incorporated into the lotion that absorb heat from the skin and melt. The components have a relatively high heat of fusion which is defined in the '564 application as the heat absorbed by unit of mass of a solid chemical element at its melting point in order to convert the solid into a liquid at the same temperature. The '564 application states that the relatively high heat of fusion facilitates the absorption of heat from the skin to aid in melting the solid ingredient when applied to the skin, thereby cooling the skin temperature.

The use of phase change agents to impart cooling in tissues is disclosed, for instance, in PCT Patent Application No. PCT/IB2009/051515 entitled "Tissue Products having a Cooling Sensation When Contacted with Skin". The '515 application discloses the use of a phase change agent between multiple layers of a dry tissue web with a separate hydrophobic lotion layer on the exterior surfaces of the tissue product to provide a cooling sensation. This approach is problematic since components of the hydrophobic lotion can migrate into the hydrophobic phase change agent and disrupt its ability to cool. Alternatively, the phase change agent can migrate into the lotion on the exterior of the tissue and may cause irritation to the skin.

Therefore, a need exists for a means to effectively hold a phase change agent on or within a substrate, such as a tissue, such that it will cool the skin without allowing irritation to the skin. There also exists a need for a substrate, such as a tissue containing the composition, such that the composition can be delivered to the nose to moisturize, cool and soothe irritated noses, while holding this phase change agent within the substrate, keeping it from irritating skin.

SUMMARY

Generally, dry wiping products and particularly dry substrates that, when held against the skin, can provide a cooling sensation are disclosed. In one embodiment, for instance, the substrate may be a facial tissue. The facial tissue can be used to provide comfort to a user's nose. For example, when suffering from the common cold, a person's nose can become inflamed and sore. In one embodiment, a tissue product that can not only be used to wipe one's nose, but can also provide the nose with a cooling sensation giving comfort and relief is disclosed.

The present disclosure is also related to a temperature change composition made of a structured emulsion containing a phase change material, a crystalline initiator, a carrier, and a surfactant. The temperature change composition undergoes a phase change at a temperature between about 20° C. and 32° C. for cooling the skin during use of the dry tissue or similar dry wiping product. Use of a structured emulsion helps to transfer the composition to the skin but limits or eliminates contacting of the phase change material with the skin of the user and/or transferring to the skin and/or wicking from the product. Thus, the structured emulsion can reduce irritation and prevent removal of the phase change agents from the product prior to use.

The structured emulsion for use with the temperature change composition may be selected from various types of structured emulsion including, but not limited to, an alpha-phase emulsion, a discontinuous cubic (micellar cubic) emulsion, a hexagonal phase emulsion, a lamellar emulsion, a bicontinuous cubic emulsion, a reverse hexagonal emulsion, an inverse cubic emulsion, or a d-phase emulsion. Desirably, the structured emulsion is a d-phase emulsion.

The phase change agent incorporated into the temperature change composition can vary depending upon the particular application and the desired result. The phase change agent, for instance, may be an oil soluble and hydrophobic material. Examples of phase change agents include hydrocarbons, waxes, oils, natural butters, fatty acids, fatty acid esters, dibasic acids, dibasic esters, 1-halides, primary alcohols, aromatic compounds, anhydrides, ethylene carbonates, polyhydric alcohols, and mixtures thereof. In one embodiment, for instance, a plurality of phase change agents can be incorporated into the temperature change composition. Particular examples of phase change agents well suited for use in the present disclosure include tricaprin, parrafin, nonadecane, octadecane, stearyl heptanoate, lauryl lactate, lauryl alcohol, capric acid, caprylic acid, cetyl babassuate, *mangifera indica* (mango) seed butter, *theobroma cacao* (cocoa) seed butter, *butyrospermum parkii* butter, Di-$C_{12\text{-}15}$ Alkyl Fumarate, stearyl caprylate, cetyl lactate, cetyl acetate, $C_{24\text{-}28}$ alkyl methicone, glyceryl dilaurate, stearamidopropyl PG-dimonium chloride phosphate, jojoba esters, and combinations thereof.

The phase change component may be present in an amount between about 1% by weight of the temperature change composition and about 99.9% by weight of the temperature change composition, more desirably between about 20% by weight of the temperature change composition and about 90% by weight of the temperature change composition, and even more desirably between about 50% by weight of the temperature change composition and about 80% by weight of the temperature change composition.

In an exemplary embodiment, the crystalline initiator is selected from fatty alcohols, fatty acids, esters, sugars, salts, crystalline and microcrystalline waxes, microcrystalline triglycerides, and combinations thereof.

Typically, the crystalline initiator may be present in an amount between about 0.1% by weight of the temperature change composition and about 30% by weight of the temperature change composition, more desirably from about 1% by weight of the temperature change composition to about 25% by weight of the temperature change composition, and even more desirably from about 2% by weight of the temperature change composition to about 20% by weight of the temperature change composition.

The temperature change composition also includes a carrier. Desirably, the carrier may be selected from water, glycerin, diglycerin, glycerin derivatives, glycols, glycol derivatives, sugars, ethoxylated and/or propoxylated esters and ethers, urea, sodium PCA, alcohols, ethanol, isopropyl alcohol, and combinations thereof.

Typically, the temperature change compositions may contain a carrier in an amount from about 1% by weight of the temperature change composition to about 40% by weight of the temperature change composition, more typically from about 2% by weight of the temperature change composition to about 25% by weight of the temperature change composition.

The temperature change composition also contains a surfactant. Examples of suitable additional surfactants include, for example, anionic surfactants, cationic surfactants, amphoteric surfactants, zwitterionic surfactants, nonionic surfactants, and combinations thereof. Specific examples of suitable surfactants are known in the art and include those suitable for incorporation into personal care compositions and tissues. The temperature change composition may suitably include one or more surfactants in an amount from about 0.5% by weight of the temperature change composition to about 15% by weight of the temperature change composition, more desirably from about 1% by weight of the temperature change composition to about 15% by weight of the temperature change composition, and even more desirably from about 2% by weight of the temperature change composition to about 7% by weight of the temperature change composition.

The dry substrate may be a product that is made from at least one web of fibers, such as pulp fibers alone or in combination with synthetic fibers. The temperature change composition may be present on at least one side of the web.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeated use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

Dry, as used herein to describe tissue or wiping products, means that the product is supplied without any moisture beyond the equilibrium moisture that is generally associated with the product. The "equilibrium moisture" is the moisture that the sheet contains when exposed to ambient conditions for extended periods of time. The equilibrium moisture within the sheet will not change with time at the same relative humidity and temperature. The dry products will have equilibrium moisture contents typically of less than 15%, such as less than 10% such as from about 3% to about 8% under most ambient conditions that are encountered during routine use of the product.

The heat absorption factor, as used herein, expressed in $J/m^2$ is defined as the product of the heat of fusion of the cooling composition expressed in J/gram and the application rate of the cooling composition applied to the tissue product expressed in gsm.

Latent heat of fusion and melting points are determined by differential scanning calorimetry (DSC). Melting point, as defined herein, refers to the peak melt temperature as determined by DSC. Samples may be analyzed on a TA Instruments DSC 2920 Modulated DSC (Standard Cell) using the following experimental procedure: Approximately 5 mg of the respective material was weighed to the nearest 0.1 mg. Samples are run in the temperature interval from $-50°$ C. to $100°$ C. with a heating/cooling rate of $10°$ C./min in an inert gas ($N_2$) atmosphere. The heat of fusion ($\Delta H_f$) is computed from the integral under the respective melting peak, with the reported results being the average value from 3 heating/cooling cycles.

The present disclosure is generally directed to dry wiping products, such as dry tissue products, that have improved perceived benefits. In particular, wiping products made in accordance with the present disclosure, when in contact with the skin, can provide a cooling sensation and feeling. The cooling sensation can, for instance, provide comfort and a soothing feeling to irritated skin. It is also found, that when used with a bath tissue, cooling can also evoke a sensation of wetness which can lead to a perception of improved cleaning. In one embodiment, the wiping product can be designed to provide a cooling sensation while transferring the composition to the skin but limiting or eliminating the contact of the phase change material from the skin of the user.

In one embodiment, for instance, the present disclosure is directed to a dry wiping product, such as a facial tissue product, that contains a temperature change composition. The temperature change composition includes at least one phase change material that undergoes a phase change when elevated in temperature. The phase change material, for example, can have a relatively high heat of fusion which allows it to absorb great amounts of thermal energy and to regulate to a lower temperature than the environment. In particular, when the wiping product is heated, such as being in contact with one's skin, the phase change material quickly warms to its melting point. Due to the high heat of fusion, significant amounts of heat can then be absorbed while the phase change material is melted. In turn, a cooling sensation is provided to the skin of the user.

Figure 1:
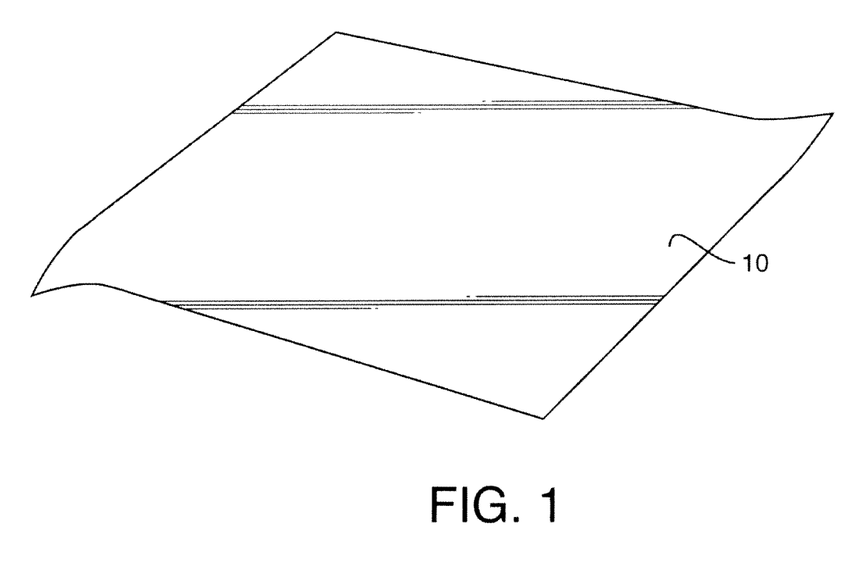
FIG. 1 is a perspective view of one embodiment of a wiping product made in accordance with the present disclosure.

Referring to FIG. 1, one embodiment of a tissue product 10 made in accordance with the present disclosure is shown. The tissue product 10 can be any suitable base sheet made from various different types of fiber furnishes. The tissue product 10 can also be a single ply product or can contain multiple tissue webs laminated together.

Tissue webs that may be used to construct the tissue product 10, for instance, can generally contain pulp fibers either alone or in combination with other fibers. Each tissue web can generally have a bulk density of at least 2 cc/g, such as at least 3 cc/g.

Fibers suitable for making tissue webs contain any natural or synthetic cellulosic fibers including, but not limited to, non-woody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898 issued Dec. 27, 1988 to Laamanen et al.; U.S. Pat. No. 4,594,130 issued Jun. 10, 1986 to Chang et al.; and U.S. Pat. No. 3,585,104 issued Jun. 15, 1971 to Kleinert. Useful fibers can also be produced by anthraquinone pulping, exemplified by U.S. Pat. No. 5,595,628 issued Jan. 21, 1997 to Gordon et al.

A portion of the fibers, such as up to 50% or less by dry weight, or from about 5% to about 30% by dry weight, can be synthetic fibers such as rayon, polyolefin fibers, polyester fibers, bicomponent sheath-core fibers, multi-component binder fibers, and the like. An exemplary polyethylene fiber is Pulpex®, available from Hercules, Inc. (Wilmington, Del.). Any known bleaching method can be used. Synthetic cellulose fiber types include rayon in all its varieties and other fibers derived from viscose or chemically-modified cellulose. Chemically treated natural cellulosic fibers can be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

Other papermaking fibers that can be used in the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a tissue web can also be utilized in the present disclosure. For example, a papermaking process of the present disclosure can utilize creping, wet creping, double creping, embossing, wet pressing, air pressing, through-air drying, creped through-air drying, uncreped through-air drying, hydroentangling, air laying, as well as other steps known in the art.

The tissue web may be formed from a fiber furnish containing pulp fibers in an amount of at least about 50% by weight, such as at least about 60% by weight, such as at least about 70% by weight, such as at least about 80% by weight, such as at least about 90% by weight, such as 100% by weight.

Also suitable for products of the present disclosure are tissue sheets that are pattern densified or imprinted, such as the tissue sheets disclosed in any of the following U.S. Pat. No. 4,514,345 issued on Apr. 30, 1985 to Johnson et al.; U.S. Pat. No. 4,528,239 issued on Jul. 9, 1985 to Trokhan; U.S. Pat. No. 5,098,522 issued on Mar. 24, 1992 to Smurkoski et al.; U.S. Pat. No. 5,260,171 issued on Nov. 9, 1993 to Smurkoski et al.; U.S. Pat. No. 5,275,700 issued on Jan. 4, 1994 to Trokhan; U.S. Pat. No. 5,328,565 issued on Jul. 12, 1994 to Rasch et al.; U.S. Pat. No. 5,334,289 issued on Aug. 2, 1994 to Trokhan et al.; U.S. Pat. No. 5,431,786 issued on Jul. 11, 1995 to Rasch et al.; U.S. Pat. No. 5,496,624 issued on Mar. 5, 1996 to Steltjes, Jr. et al.; U.S. Pat. No. 5,500,277 issued on Mar. 19, 1996 to Trokhan et al.; U.S. Pat. No. 5,514,523 issued on May 7, 1996 to Trokhan et al.; U.S. Pat. No. 5,554,467 issued on Sep. 10, 1996 to Trokhan et al.; U.S. Pat. No. 5,566,724 issued on Oct. 22, 1996 to Trokhan et al.; U.S. Pat. No. 5,624,790 issued on Apr. 29, 1997 to Trokhan et al.; and U.S. Pat. No. 5,628,876 issued on May 13, 1997 to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

The tissue web can also be formed without a substantial amount of inner fiber-to-fiber bond strength. In this regard, the fiber furnish used to form the base web can be treated with a chemical debonding agent. The debonding agent can be added to the fiber slurry during the pulping process or can be added directly to the headbox. Suitable debonding agents that may be used in the present disclosure include cationic debonding agents such as fatty dialkyl quaternary amine salts, mono fatty alkyl tertiary amine salts, primary amine salts, imidazoline quaternary salts, silicone quaternary salt and unsaturated fatty alkyl amine salts. Other suitable debonding agents are disclosed in U.S. Pat. No. 5,529,665 issued on Jun. 25, 1996 to Kaun which is incorporated herein by reference. In particular, Kaun '665 discloses the use of cationic silicone compositions as debonding agents.

In one embodiment, the debonding agent used in the process of the present disclosure is an organic quaternary ammonium chloride and, particularly, a silicone-based amine salt of a quaternary ammonium chloride. For example, the debonding agent can be PROSOFT® TQ1003, marketed by the Hercules Corporation. The debonding agent can be added to the fiber slurry in an amount from about 1 kg per metric tonne to about 10 kg per metric tonne of fibers present within the slurry.

In an alternative embodiment, the debonding agent can be an imidazoline-based agent. The imidazoline-based debonding agent can be obtained, for instance, from the Witco Corporation (Greenwich, Conn.). The imidazoline-based debonding agent can be added in an amount of between 2 kg per metric tonne to about 15 kg per metric tonne.

In one embodiment, the debonding agent can be added to the fiber furnish according to a process as disclosed in PCT Application having an International Publication No. WO 99/34057 filed on Dec. 17, 1998 or in PCT Published Application having an International Publication No. WO 00/66835 filed on Apr. 28, 2000, which are both incorporated herein by reference. In the above publications, a process is disclosed in which a chemical additive, such as a debonding agent, is adsorbed onto cellulosic papermaking fibers at high levels. The process includes the steps of treating a fiber slurry with an excess of the chemical additive, allowing sufficient residence time for adsorption to occur, filtering the slurry to remove unadsorbed chemical additives, and redispersing the filtered pulp with fresh water prior to forming a nonwoven web.

Optional chemical additives may also be added to the aqueous papermaking furnish or to the formed embryonic web to impart additional benefits to the product and process and are not antagonistic to the intended benefits of the dry substrate. The following materials are included as examples of additional chemicals that may be applied to the web along with the temperature change composition. The chemicals are included as examples and are not intended to limit the scope of the invention. Such chemicals may be added at any point in the papermaking process, including being added simultaneously with the additive composition in the pulp making process, wherein said additive or additives are blended directly with the additive composition.

Additional types of chemicals that may be added to the paper web include, but are not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin E, silicone, lotions in general, and the like, may also be incorporated into the finished products.

In general, the products can be used in conjunction with any known materials and chemicals that are not antagonistic to its intended use. Examples of such materials include, but are not limited to, odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients, and the like.

Tissue webs that may be treated with the temperature change composition may include a single homogenous layer of fibers or may include a stratified or layered construction. For instance, the tissue web ply may include two or three layers of fibers. Each layer may have a different fiber composition.

Each of the fiber layers contains a dilute aqueous suspension of papermaking fibers. The particular fibers contained in each layer generally depends upon the product being formed and the desired results. In one embodiment, for instance, a middle layer contains southern softwood kraft fibers either alone or in combination with other fibers, such as high yield fibers. The outer layers, on the other hand, can contain softwood fibers, such as northern softwood kraft.

In an alternative embodiment, the middle layer may contain softwood fibers for strength, while the outer layers may contain hardwood fibers, such as eucalyptus fibers, for a perceived softness.

The basis weight of tissue webs can vary depending upon the final product. For example, the process may be used to produce facial tissues, bath tissues, paper towels, industrial wipers, and the like. In general, the basis weight of the tissue products may vary from about 10 gsm to about 80 gsm, such as from about 20 gsm to about 60 gsm. For bath and facial tissues, for instance, the basis weight may range from about 10 gsm to about 60 gsm. For paper towels, on the other hand, the basis weight may range from about 25 gsm to about 80 gsm.

The tissue web bulk may also vary from about 2 cc/g to 20 cc/g, such as from about 5 cc/g to 15 cc/g. The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc. (Newberg, Oreg.). The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

In multiple ply products, the basis weight of each tissue web present in the product can also vary. In general, the total basis weight of a multiple ply product will typically be the same as indicated above, such as from about 20 gsm to about 80 gsm. Thus, the basis weight of each ply can be from about 5 gsm to about 60 gsm, such as from about 10 gsm to about 40 gsm. In accordance with the present disclosure, the tissue product 10 contains a temperature change composition for imparting a cooling sensation to the skin of a user.

The temperature change composition for imparting a cooling sensation to the skin of a user is constructed of a structured emulsion containing a phase change material, a crystalline initiator, a carrier, and a surfactant. The temperature change composition undergoes a phase change at a temperature between about 20° C. and 32° C. for cooling the skin during use of the dry tissue or similar dry wiping product. Phase change materials are known to cause irritation as it easily penetrates skin. Use of a structured emulsion helps to transfer the composition to the skin but limits or eliminates contacting of the phase change material with the skin of the user and/or transferring to the skin and/or wicking from the product. Thus, the structured emulsion can reduce irritation caused by the phase change materials from the product prior to use.

The structured emulsion for use with the temperature change composition may be selected from various types of structured emulsion including, but not limited to, an alpha-phase emulsion, a discontinuous cubic (micellar cubic) emulsion, a hexagonal phase emulsion, a lamellar emulsion, a bicontinuous cubic emulsion, a reverse hexagonal emulsion, an inverse cubic emulsion, and a d-phase emulsion.

To achieve delivery of the cooling sensation, a temperature change composition is desirably in the form of an oil phase dispersed in a single phase cubic liquid crystal or "d-phase" concentrated emulsion. Preferably, the oil phase is present in the composition in an amount from 50-100%, more preferably from 60-90% and most preferably from 65-85%. The amount of oil added is at a desirable level when the emulsion micelles shift from a spherical to a more polygonal shape. That is, the droplets increase in size by internally packing such that they push up against one another and at the point of contact with adjacent micelles the pressure exerted creates an equilibrium plateau instead of the normal curvature expected in a micellar sphere.

Structured emulsions such as d-phase emulsions are well known in the art. However, d-phase emulsions are thought to be efficient at delivering actives and molecules into the skin. For example, interaction between liquid crystalline phase and the skin lipids is thought to enhance the transdermal delivery of a lipophilic entity, octadecenedioc acid, within a crystalline emulsion. (Otto, A., Du Plessis, J. and Weichers, J. W. Formulation effects of topical emulsions on transdermal and dermal delivery. Intl. J. of Cosmetic Science. 31, 11-12 (2009). Therefore, it would be expected that including a hydrophobic phase change material within a d-phase emulsion would provide better transfer of the phase change material and cause greater irritation.

However, use of the temperature change composition comprising a structured emulsion, such as a d-phase emulsion, disclosed herein helps to transfer the composition to the skin but unexpectedly limits or eliminates contacting of the phase change material with the skin of the user and/or transferring to the skin and/or wicking from the product. As evidenced by the Examples discussed herein, use of a crystalline initiator within the d-phase emulsion provides a temperature change composition that is cooling, but is not irritating to the skin. Thus, the structured emulsion can reduce irritation and prevent removal of the phase change agents from the product prior to use. With prior temperature change compositions, disclosed in for example, PCT Patent Application No. PCT/IB2009/051515 entitled "Tissue Products having a Cooling Sensation When Contacted with Skin," the phase change materials transfer to the skin and cause irritation.

The temperature change composition can be incorporated into the tissue product 10 using any suitable method or technique. For example, the temperature change composition can be sprayed onto the tissue product, extruded onto the tissue product, or printed onto the tissue product using, for instance, flexographic printing, direct gravure printing, or indirect gravure printing. In still another embodiment, the temperature change composition can be applied to the tissue product using any suitable coating equipment, such as a knife coater, UFD coater, or slot coater. As the temperature change composition is solid at room temperature in one embodiment, it may be desirable to melt the composition prior to application to the tissue web. The application of such molten materials to a finished tissue web is well known in the art. At times it may also be advantageous to cool the web directly after application of the molten phase change material, especially when the treated product is wound into a spirally wound roll either for a finished product or for further processing. The cooling of the web below the melting point of the phase change material reduces the potential of the spirally wound web from becoming "blocked". "Blocked," as used herein, refers to the tendency of adjacent facing sheets in the spirally wound roll to adhere to each other and restrict the ability to unwind the web from the spirally wound roll.

The temperature change composition includes at least one phase change material that undergoes a phase change when heated which, in turn, provides a cooling sensation to the skin. In general, a phase change material includes any substance that has the capability of absorbing or releasing thermal energy to reduce or eliminate heat flow at or within a temperature stabilizing range. The temperature stabilizing range may include a particular transition temperature or range of transition temperatures. A phase change material used preferably will be capable of altering a flow of thermal energy during a time when the phase change material is absorbing or releasing heat, typically as the phase change material undergoes a transition between two states (e.g., liquid and solid states, liquid and gaseous states, solid and gaseous states, or two solid states). This action is typically transient, meaning it will occur until a latent heat of the phase change material is absorbed or released during a heating or cooling process. Thermal energy may be stored or removed from the phase change material, and the phase change material typically can be effectively recharged by a source of heat or cold. The temperature change compositions exhibit a phase change at temperatures between about 23° C. and about 35° C. such as to be appropriate for use in cooling skin. In other embodiments materials may be chosen with transition temperatures between about 23° C. and about 32° C., between about 26° C. and about 32° C., or within any other suitable range. The phase change temperature is selected such that the phase change occurs between the ambient temperature of the product and the external temperature of the user's skin.

The temperature change composition may contain a mixture of phase change materials that have a mixture of transition temperatures. When a mixture of phase change materials is used, the components can be selected so as to have a collective melting point within the above mentioned limits. In some cases the melting points of the individual phase change materials comprising the temperature change composition may lie outside the melting point limits for the phase change temperature of the temperature change composition. However, the mixture of phase change materials will display a phase change within the desired temperature limits. When the temperature change composition is held against the skin either directly or indirectly, the composition warms to the temperature of the skin from room temperature. The phase change material then melts at its specified phase change temperature. That melting requires heat, which is taken from the skin, imparting a feeling of cooling. Once the material is melted, the cooling sensation dissipates. Having a range of phase change temperatures (melting points in this case) of the phase change materials may extend the range of temperatures where cooling is felt. In one example, a combination of phase change materials having phase change temperatures at 18° C., 26° C., and 35° C. are combined to create a temperature change composition having a melting point between 23° C. and 32° C.

Suitable phase change materials include, by way of example and not by limitation, encapsulated phase change powder, (e.g., LURAPRET, a purified, encapsulated paraffin available from BASF and MPCM 43-D available from Microtek Laboratories), hydrocarbons (e.g., straight chain alkanes or paraffinic hydrocarbons, branched-chain alkanes, unsaturated hydrocarbons, halogenated hydrocarbons, and alicyclic hydrocarbons), waxes, natural butters, fatty acids, fatty acid esters, dibasic acids, dibasic esters, 1-halides, primary alcohols, aromatic compounds, anhydrides (e.g., stearic anhydride), ethylene carbonate, polyhydric alcohols (e.g., 2,2-dimethyl-1,3-propanediol, 2-hydroxymethyl-2-methyl-1,3-propanediol, pentaerythritol, dipentaerythritol, pentaglycerine, tetramethylol ethane, neopentyl glycol, tetramethylol propane, monoaminopentaerythritol, diaminopentaerythritol, and tris(hydroxymethyl)acetic acid), polymers (e.g., polyethylene, polyethylene glycol, polypropylene, polypropylene glycol, polytetramethylene glycol, and copolymers, such as polyacrylate or poly(meth)acrylate with alkyl hydrocarbon side chain or with polyethylene glycol side chain and copolymers comprising polyethylene, polyethylene glycol, polypropylene, polypropylene glycol, or polytetramethylene glycol), and mixtures thereof. Two well suited phase change materials are stearyl heptanoate and n-octadecane. Other desirable phase change materials include tricaprin, parrafin, nonadecane, octadecane, stearyl heptanoate, lauryl lactate, lauryl alcohol, capric acid, caprylic acid, cetyl babassuate, *mangifera indica* (mango) seed butter, *theobroma cacao* (cocoa) seed butter, butyrospermum parkii butter, Di-$C_{12-15}$ Alkyl Fumarate, stearyl caprylate, cetyl lactate, cetyl acetate, $C_{24-28}$ alkyl methicone, glyceryl dilaurate, stearamidopropyl PG-dimonium chloride phosphate, jojoba esters, and combinations thereof.

As described above, in one embodiment, the temperature change composition may contain a mixture of two or more phase change materials. In one particular embodiment, the temperature change composition contains a mixture of stearyl heptanoate and n-octadecane.

Phase change materials may include phase change materials in a non-encapsulated form and phase change materials in an encapsulated form. A phase change material in a non-encapsulated form may be provided as a solid in a variety of forms (e.g., bulk form, powders, pellets, granules, flakes, paste, and so forth) or as a liquid in a variety of forms (e.g., molten form, dissolved in a solvent, and so forth).

Another aspect of the temperature change compositions is the heat of fusion of the temperature change composition comprising the phase change materials. The temperature change compositions can have heats of fusion of at least about 100 J/g, such as at least about 120 J/g, such as at least about 145 J/g, such as at least about 165 J/g, such as at least about 190 J/g. For instance, in one embodiment, the temperature change composition contains a hydrocarbon as the phase change material, such as a straight chain hydrocarbon. The hydrocarbon, for instance, may contain more than about 12 carbon atoms in the chain, such as from about 18 carbon atoms to about 19 carbon atoms in the chain. Particular examples of phase change materials include, for instance, octadecane (heat of fusion of about 213 J/g), nonadecane, stearyl heptanoate, and mixtures thereof.

The phase change materials can be contained in the temperature change composition in an amount from about 1% by weight of the temperature change composition to 99% by weight of the temperature change composition, such as from about 5% by weight of the temperature change composition to about 90% by weight of the temperature change composition. For example, in particular embodiments, the phase change materials may be present in the temperature change composition in an amount from about 50% by weight of the temperature change composition to about 80% by weight of the temperature change composition.

Desirably, the crystalline initiator is selected from fatty alcohols, fatty acids, esters, sugars, salts, crystalline and microcrystalline waxes, microcrystalline triglycerides, and combinations thereof.

Typically, the crystalline initiator is present in an amount between about 0.1% by weight of the temperature change composition and about 20% by weight of the temperature change composition more typically from about 1% by weight of the temperature change composition to about 15% by weight of the temperature change composition, and even more typically from about 2% by weight of the temperature change composition to about 10% by weight of the temperature change composition.

As discussed above, the temperature change composition includes a carrier. Desirably, the carrier is selected from water, glycerin, diglycerin, glycerin derivatives, glycols, glycol derivatives, sugars, ethoxylated and/or propoxylated esters and ethers, urea, sodium PCA, alcohols, ethanol, isopropyl alcohol, or combinations thereof.

Typically, the temperature change compositions contain a carrier in an amount from about 1% by weight of the temperature change composition to about 40% by weight of the temperature change composition, more typically from about 2% by weight of the temperature change composition to about 25% by weight of the temperature change composition.

The temperature change composition also contains a surfactant. Examples of suitable surfactants to form a structured emulsion include sugar esters and their derivatives, sucrose esters, polyglyceryl esters, sorbitan esters, fatty acid esters, alkylpolyglucosides, and combinations thereof. Desirable surfactants include sorbitan stearate, sorbityl laurate, sucrose palmitate, sucrose cocoate, cetearyl olivate, sorbitan olivate, cetearyl glucoside, coco glucoside, myristyl glucoside, isostearyl glucoside, and combinations thereof. The temperature change composition may suitably include one or more surfactants in an amount from about 0.5% by weight of the temperature change composition to about 15% by weight of the temperature change composition.

Typically, the temperature change composition is thermally reversible. Thus the temperature change composition is such that at below a transition temperature, the composition exists in a solid or hard gel state. At a temperature of at least 50° C., the composition exists in a flowable gel state, but maintains a viscosity range of about 500 cps to about 20,000 cps, more desirably a range of about 1000 cps to about 10,000 cps, more desirably a range of about 2000 cps to about 6000 cps.

Having a thermally reversible temperature change composition is very important. A temperature change composition which is thermally reversible allows the product to be exposed to extreme temperatures during transportation of the product and still work effectively in the home when used by a consumer. The thermally reversible temperature change composition disclosed herein will change from a solid state to liquid state and back to a solid as the temperatures change. Thus, the phase change materials to provide a cooling effect are still available after long periods of storage and transportation at various temperatures. Previous temperature change compositions, disclosed in for example, PCT Patent Application No. PCT/IB2009/051515 entitled "Tissue Products having a Cooling Sensation When Contacted with Skin" are not thermally reversible and do not provide these benefits.

The temperature change composition uses a phase change material to provide a measurable cooling benefit but also uses a delivery vehicle such that the phase change material is entrapped within an emulsion so it can cool and not irritate skin. It consists of two distinctly different phases, a dispersed phase and a continuous phase, emulsified together to create an d-phase emulsion.

To prepare the temperature change composition disclosed herein, a continuous phase is prepared by mixing together a surfactant and carrier. A phase change material is mixed together with a crystalline initiator to prepare a second phase. The second phase is added to the continuous phase and the second phase is dispersed within the continuous phase.

Because the oil is the internal phase of the d-phase emulsion, the temperature change composition has increased absorbency when applied to the substrate. The temperature change composition can incorporate water from secretions into the polar phase of the emulsion. Therefore, absorption of water and similar aqueous secretions is nearly instantaneous. Typically, the dry tissue products using the temperature change compositions can absorb a single drop of water placed on the treated side of tissue within 90 seconds, within 60 seconds, within 45 seconds, more typically absorbing a single drop of water within 30 seconds, and even more typically absorbing a single drop of water within 20 seconds.

Additionally, in production, cleaning up the machinery and workspace used to produce traditional lotion tissue can be lengthy as the formulations form a waxy solid at temperatures below their melting point (typically <50-60° C.) which needs to be scraped or melted off of surfaces or otherwise removed. The temperature change composition contains a hydrophilic phase in addition to the hydrophobic phase. Thus, the temperature change composition can easily be cleaned up with water and minimal labor.

Another important factor is the heat absorption factor of the products. The heat absorption factor, expressed in $J/m^2$, is the product of the heat of fusion of the temperature change composition expressed in J/gram and the application rate of the temperature change composition applied to the tissue product expressed in gram per meter squared (gsm). The heat absorption factor of the products can be at least about 500 $J/m^2$, such as at least about 1000 $J/m^2$ such as from about 1000 $J/m^2$ to about 4000 $J/m^2$ or greater. For many applications, the temperature change composition can be applied to a tissue web such that the phase change materials are present on the web in an amount from about 4 gsm to about 40 gsm.

The temperature change composition may take a variety of forms including, without limitation, aqueous solutions, gels, balms, lotions, suspensions, creams, milks, salves, ointments, sprays, foams, solid sticks, and the like.

Also, as typical lotion tissues consist primarily of oils and waxes, it is difficult, if not impossible, to incorporate skin health ingredients of a hydrophilic nature into the formulation at adequate amounts to see the associated benefit of the ingredients. The temperature change composition can include either hydrophilic or hydrophobic skin health ingredients as it contains both a hydrophilic continuous phase and a hydrophobic dispersed phase within the emulsion.

Examples of other skin health ingredients that may be included within the temperature change composition are emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, anti-wrinkle actives, soothing agents, antioxidants, and the like.

Thus, the temperature change compositions may further optionally include one or more emollients, which typically act to soften, soothe, and otherwise lubricate and/or moisturize the skin. Suitable emollients that can be incorporated into the compositions include oils such as natural oils such as jojoba, sunflower, safflower, and the like, synthetic based oils such as petrolatum, mineral oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, glycerol esters and derivatives, propylene glycol esters and derivatives, fatty acid esters and derivatives, alkoxylated carboxylic acids, alkoxylated alcohols, and combinations thereof.

Ethers such as eucalyptol, cetearyl glucoside, dimethyl isosorbic polyglyceryl-3 cetyl ether, polyglyceryl-3 decyltetradecanol, propylene glycol myristyl ether, and combinations thereof, can also suitably be used as emollients.

The temperature change composition may include one or more emollients in an amount from about 0.01% by weight of the temperature change composition to about 70% by weight of the temperature change composition, more desirably from about 0.05% by weight of the temperature change composition to about 50% by weight of the temperature change composition, and even more desirably from about 0.1% by weight of the temperature change composition to about 40% by weight of the temperature change composition.

Optionally, one or more viscosity enhancers may be added to the temperature care composition to increase the viscosity, to help stabilize the composition, such as when the composition is incorporated into a personal care product, thereby reducing migration of the composition and improve transfer to the skin. Suitable viscosity enhancers include polyolefin resins, lipophilic/oil thickeners, polyethylene, silica, silica silylate, silica methyl silylate, colloidal silicone dioxide, cetyl hydroxy ethyl cellulose, other organically modified celluloses, PVP/decane copolymer, PVM/MA decadiene crosspolymer, PVP/eicosene copolymer, PVP/hexadecane copolymer, clays, carbomers, acrylate based thickeners, surfactant thickeners, and combinations thereof.

The temperature change composition may include one or more viscosity enhancers in an amount from about 0.01% by weight of the temperature change composition to about 25% by weight of the temperature change composition, more desirably from about 0.05% by weight of the temperature change composition to about 10% by weight of the temperature change composition, and even more desirably from about 0.1% by weight of the temperature change composition to about 10% by weight of the temperature change composition.

The temperature change composition may optionally further contain rheology modifiers. Rheology modifiers may help increase the melt point viscosity of the composition so that the composition readily remains on the surface of a personal care product.

Suitable rheology modifiers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, humectant/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/humectant-styrene copolymers, styrene-ethylene/propylene-styrene copolymers, (styrene-butadiene) n-polymers, (styrene-isoprene) n-polymers, styrene-butadiene copolymers, and styrene-ethylene/propylene copolymers, and combinations thereof. Specifically, rheology enhancers such as mineral oil and ethylene/propylene/styrene copolymers, and mineral oil and humectant/ethylene/styrene copolymers are particularly desirable.

The temperature change composition can suitably include one or more rheology modifiers in an amount from about 0.1% by weight of the temperature change composition to about 10% by weight of the temperature change composition.

The temperature change composition may optionally further contain humectants. Examples of suitable humectants include glycerin, glycerin derivatives, 1,3-propanediol, sodium hyaluronate, betaine, amino acids, glycosaminoglycans, honey, sugar alcohols, sorbitol, glycols, polyols, sugars, hydrogenated starch hydrolysates, salts of PCA, lactic acid, lactates, and urea. A particularly preferred humectant is glycerin. The temperature change composition may suitably include one or more humectants in an amount from about 0.05% by weight of the temperature change composition to about 50% by weight of the temperature change composition.

The temperature change composition may optionally further contain film formers. Examples of suitable film formers include lanolin derivatives (e.g., acetylated lanolins), superfatted oils, cyclomethicone, cyclopentasiloxane, dimethicone, synthetic and biological polymers, proteins, quaternary ammonium materials, starches, gums, cellulosics, polysaccharides, albumen, acrylates derivatives, IPDI derivatives, and the like. The composition may suitably include one or more film formers in an amount from about 0.01% by weight of the temperature change composition to about 20% by weight of the temperature change composition.

The temperature change composition may optionally further contain slip modifiers. Examples of suitable slip modifiers include bismuth oxychloride, iron oxide, mica, surface treated mica, ZnO, $ZrO_2$, silica, silica silyate, colloidal silica, attapulgite, sepiolite, starches (i.e. corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, aluminum oxide, silicone resin, barium sulfate, calcium carbonate, cellulose acetate, polymethyl methacrylate, polymethylsilsequioxane, talc, tetrafluoroethylene, silk powder, boron nitride, lauroyl lysine, synthetic oils, natural oils, esters, silicones, glycols, and the like. The composition of the present disclosure may suitably include one or more slip modifiers in an amount from about 0.01% by weight of the temperature change composition to about 20% by weight of the temperature change composition.

The temperature change composition may also optionally contain surface modifiers. Examples of suitable surface modifiers include silicones, quaternium materials, powders, salts, peptides, polymers, clays, and glyceryl esters. The composition of the present disclosure may suitably include one or more surface modifiers in an amount from about 0.01% by weight of the temperature change composition to about 20% by weight of the temperature change composition.

The temperature change composition may also optionally contain skin protectants. Examples of suitable skin protectants include ingredients referenced in SP Monograph (21 CFR part 347). Suitable skin protectants and amounts include those set forth in SP Monograph, Subpart B—Active Ingredients Sec 347.10: (a) Allantoin, 0.5 to 2%, (b) Aluminum hydroxide gel, 0.15 to 5%, (c) Calamine, 1 to 25%, (d) Cocoa butter, 50 to 100%, (e) Cod liver oil, 5 to 13.56%, in accordance with 347.20(a)(1) or (a)(2), provided the product is labeled so that the quantity used in a 24-hour period does not exceed 10,000 U.S.P. Units vitamin A and 400 U.S.P. Units cholecalciferol, (f) Colloidal oatmeal, 0.007% minimum; 0.003% minimum in combination with mineral oil in accordance with §347.20(a)(4), (g) Dimethicone, 1 to 30%, (h) Glycerin, 20 to 45%, (i) Hard fat, 50 to 100%, (j) Kaolin, 4 to 20%, (k) Lanolin, 12.5 to 50%, (l) Mineral oil, 50 to 100%; 30 to 35% in combination with colloidal oatmeal in accordance with §347.20(a)(4), (m) Petrolatum, 30 to 100%, (n) Sodium bicarbonate, (o) Topical starch, 10 to 98%, (p) White petrolatum, 30 to 100%, (q) Zinc acetate, 0.1 to 2%, (r) Zinc carbonate, 0.2 to 2%, (s) Zinc oxide, 1 to 25%.

The temperature change composition may also optionally contain quaternary ammonium materials. Examples of suitable quaternary ammonium materials include polyquaternium-7, polyquaternium-10, benzalkonium chloride, behentrimonium methosulfate, cetrimonium chloride, cocamidopropyl pg-dimonium chloride, guar hydroxypropyltrimonium chloride, isostearamidopropyl morpholine lactate, polyquaternium-33, polyquaternium-60, polyquaternium-79, quaternium-18 hectorite, quaternium-79 hydrolyzed silk, quaternium-79 hydrolyzed soy protein, rapeseed amidopropyl ethyldimonium ethosulfate, silicone quaternium-7, stearalkonium chloride, palmitamidopropyltrimonium chloride, butylglucosides, hydroxypropyltrimonium chloride, laurdimoniumhydroxypropyl decylglucosides chloride, and the like. The composition of the present disclosure may suitably include one or more quaternary materials in an amount from about 0.01% by weight of the temperature change composition to about 20% by weight of the temperature change composition.

The temperature change composition may also optionally contain additional emulsifiers. As mentioned above, the natural fatty acids, esters and alcohols and their derivatives, and combinations thereof, may act as emulsifiers in the composition. Optionally, the composition may contain an additional emulsifier other than the natural fatty acids, esters and alcohols and their derivatives, and combinations thereof. Examples of suitable emulsifiers include nonionics such as polysorbate 20, polysorbate 80, anionics such as DEA phosphate, cationics such as behentrimonium methosulfate, and the like. The composition of the present disclosure may suitably include one or more additional emulsifiers in an amount from about 0.01% by weight of the temperature change composition to about 20% by weight of the temperature change composition.

The temperature change composition may additionally include adjunct components conventionally found in pharmaceutical compositions in their art-established fashion and at their art-established levels. For example, the compositions may contain additional compatible pharmaceutically active materials for combination therapy, such as antimicrobials, antioxidants, anti-parasitic agents, antipruritics, antifungals, antiseptic actives, biological actives, astringents, keratolytic actives, local anesthetics, anti-stinging agents, anti-reddening agents, skin soothing agents, and combinations thereof. Other suitable additives that may be included in the compositions of the present disclosure include colorants, deodorants, fragrances, perfumes, emulsifiers, anti-foaming agents, lubricants, natural moisturizing agents, skin conditioning agents, skin protectants and other skin benefit agents (e.g., extracts such as aloe vera and anti-aging agents such as peptides), solvents, solubilizing agents, suspending agents, wetting agents, humectants, preservatives, pH adjusters, buffering agents, dyes and/or pigments, and combinations thereof.

Although the temperature change composition can be present on an exterior surface of the tissue product 10 as shown on FIG. 1, in one embodiment, the temperature change composition can be incorporated into the tissue product in a manner so that substantially none of the temperature change composition is present on the exterior surfaces. For instance, referring to FIG. 2, a tissue product 20 is shown that is comprised of a first tissue web 22 laminated to a second tissue web 24. As shown, positioned in between the first tissue web 22 and the second tissue web 24 is a temperature change composition 26 as described herein. By locating the temperature change composition 26 in between the tissue webs, the temperature change composition is substantially prevented from being transferred to a user's skin. When the tissue product 20, however, is held against the skin, body heat will be absorbed by the temperature change composition 26 through the tissue webs thus elevating in temperature. The increase in temperature will cause a phase change to occur in the phase change material providing a cooling sensation to the skin of the user.

In one specific embodiment the cooling tissue product is a facial tissue comprising three or more plies, two outer plies and one or more interior plies. The temperature change composition is applied to at least one of the one or more interior plies. In another embodiment, the cooling tissue product is a facial tissue comprising two plies, comprising two outer facing surfaces and two oppositely facing inner surfaces. The phase change composition is applied to one or both of the oppositely facing inner surfaces. In another embodiment, the product is a multi-ply tissue product where the phase change composition is applied selectively to the inner portion of the multi-ply product so as to minimize blocking.

Figure 2:
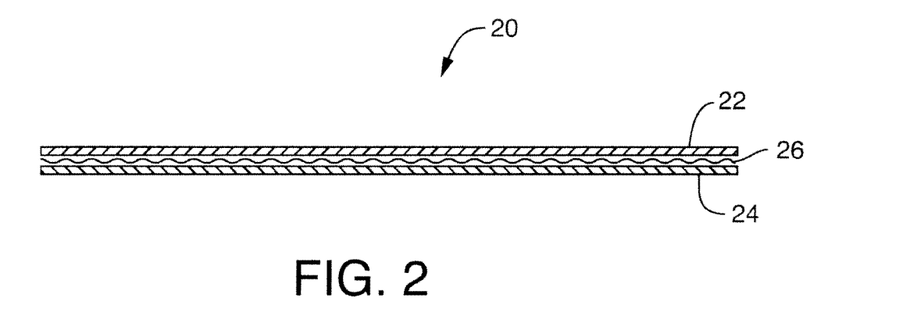
FIG. 2 is a cross-sectional view of the wiping product illustrated in FIG. 1.

In this manner, other beneficial compositions may be applied to the exterior surface of the tissue product and used in conjunction with the temperature change composition 26. For example, in one embodiment, a lotion that is intended to moisturize the skin can be present on at least one exterior surface of the tissue product and may work in conjunction with the temperature change composition. In this manner, the tissue product 20 can not only provide a cooling sensation to the user, but can also transfer a moisturizer to the skin.

In addition to lotions, any other suitable composition may also be applied to the exterior surface. For instance, in one embodiment, various softening agents may be present on the exterior surfaces of the tissue product. One example of a softening agent may contain a polysiloxane.

Figure 3:
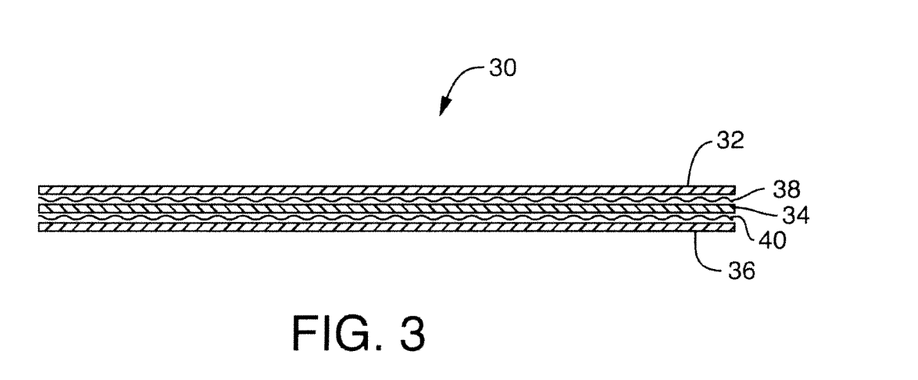
FIG. 3 is a cross-sectional view of another embodiment of a wiping product made in accordance with the present disclosure.

In addition to a 2-ply product as shown in FIG. 2, other tissue products that may included the temperature change composition can include more than two plies. For example, a 3-ply tissue product 30 is illustrated in FIG. 3. As shown, the tissue product 30 includes a middle tissue web 34 laminated to outer tissue webs 32 and 36. In accordance with the present disclosure, a temperature change composition is located in between the first tissue web 32 and the middle tissue web 34. A temperature change composition 40 is also positioned in between the middle tissue web 34 and the second outer tissue web 36.

In an alternative embodiment, the temperature change composition can also be present on one or more exterior surfaces of a tissue product. For instance, referring to FIG. 4, in one embodiment, the temperature change composition can be applied to an exterior surface of a bath tissue product 50. As shown, the bath tissue product 50 contains a spirally wound product containing individual tissue sheets 52 separated by perforation lines 54. The tissue sheets can include a first exterior surface 56 and a second exterior surface 58. Each tissue sheet may contain a single ply product or a multi-ply product. The temperature change composition may be present on the first exterior surface 56, on the second exterior surface 58, or on both exterior surfaces.

Figure 4:
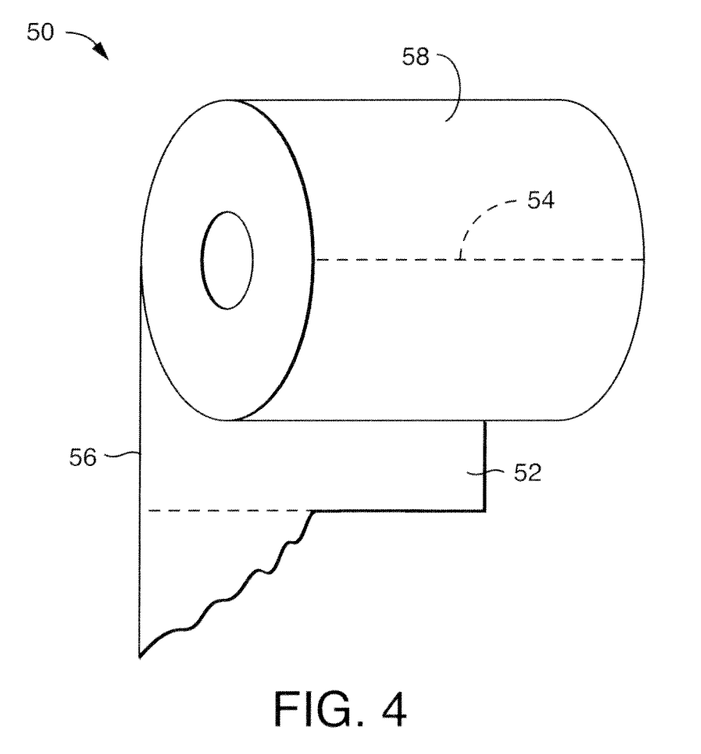
FIG. 4 is a perspective view of one embodiment of a spirally wound bath tissue product made in accordance with the present disclosure.

Applying the temperature change composition to a bath tissue product as shown in FIG. 4 may provide various unexpected benefits and advantages. For example, the temperature change composition may provide a cooling sensation that actually makes the bath tissue sheet evoke a sensation of wetness to the user. The sense of wetness can lead to a perception of improved cleaning.

When applied to a bath tissue as shown in FIG. 4, the temperature change composition may contain a moisturizer as described above so as to provide further benefits to the user.

EXAMPLES

The present disclosure may be better understood with reference to the following examples.

Example 1

Example 1, illustrated in Table 1, demonstrates a composition using a phase change material, a crystalline initiator, a surfactant, and a carrier.

TABLE 1

| Example 1 | |
|---|---|
| Ingredient | Wt. % |
| Phase A | |
| Sucrose Laurate | 3 |
| Glycerin | 19 |
| Water | 5 |
| Phase B | |
| Stearyl Heptanoate | 63 |
| Stearyl Alcohol | 10 |

First, Phase A was created by mixing the three components at 70° C. until uniform. Simultaneously, Phase B was created by mixing the two components at 70° C. until uniform. Phase B was then added to phase A with high shear mixing (5000 rpm). Once Phase B is added to Phase A, the mixture was mixed at 10,000 rpm for 5 minutes.

Example 1 produced a solid white gel that is in solid state after cooling to room temperature. A portion of the sample was rubbed on the skin of two human subjects and a considerable cooling effect was felt. This illustrates that the phase change material in combination with a crystalline initiator sets up a d-phase emulsion ideal for cooling.

Comparative Example 1

Comparative Example 1, illustrated in Table 2, demonstrates a composition created using a phase change material, a surfactant, and a carrier. No crystalline initiator was used within the comparative example.

TABLE 2

| Comparative Example 1 | |
|---|---|
| Ingredient | Wt. % |
| Phase A | |
| Sucrose Laurate | 6 |
| Glycerin | 19 |
| Water | 5 |
| Phase B | |
| Stearyl Heptanoate | 70 |

First, Phase A was created by mixing the three components at 70° C. until uniform. Phase B was then added to phase A with high shear mixing (5000 rpm). Once Phase B was added to Phase A, the mixture was mixed at 10,000 rpm for 5 minutes.

Comparative Example 1 did not produce a solid white gel. Instead, it produced a transparent gel that remained a transparent gel after cooling to room temperature. Upon application to the skin, the transparent gel did not phase change on the skin and therefore no cooling was felt. The sample was placed into a refrigerator to try to induce crystallization of the phase change material. After 2 hours, the sample was taken out of the refrigerator and allowed to acclimate to room temperature. The resultant gel was no longer transparent, but had turned into a white gel. A portion of the sample was rubbed on the skin of 2 human subjects but no cooling was felt. This illustrates that the phase change material did not set up a d-phase emulsion adequate for cooling in this delivery vehicle without a crystalline initiator.

Comparative Example 2

Comparative Example 2, illustrated in Table 3, is a composition that does not contain a phase change material, but includes a crystalline initiator. The ingredients were combined and heated to 60° C. until homogenous. The composition was cooled and produced a solid white paste at room temperature. The paste was rubbed on the skin of 2 human subjects but no cooling was felt. This illustrates that the crystalline initiator by itself does not set up a crystalline network sufficient for cooling the skin.

TABLE 3

| Comparative Example 2 | |
|---|---|
| Ingredient | Wt. % |
| Petrolatum | 60 |
| Stearyl Alcohol | 6 |

These and other modifications and variations to the appended claims may be practiced by those of ordinary skill in the art, without departing from the spirit and scope of the appended claims. In addition, it should be understood that aspects of the various embodiments may be interchanged both in whole and in part. Furthermore, those of ordinary skill in the art will appreciate that the foregoing description is by way of example only, and is not intended to limit the appended claims.

What is claimed:

1. A temperature change composition to contact the skin to cause a cooling sensation comprising a structured emulsion containing:
   a phase change material present in an amount between about 1% by weight of the temperature change composition and about 99% by weight of the temperature change composition;
   a crystalline initiator present in an amount between about 0.1% by weight of the temperature change composition and about 30% by weight of the temperature change composition;
   a carrier present in an amount between about 1% by weight of the temperature change composition and about 40% by weight of the temperature change composition; and
   a surfactant present in an amount between about 0.5% by weight of the temperature change composition and about 15% by weight of the temperature change composition;
   wherein the structured emulsion is a d-phase emulsion.

2. The temperature change composition of claim 1 wherein the temperature change composition is thermally reversible.

3. The temperature change composition of claim 1 wherein the temperature change composition is solid at room temperature and has a phase change at a temperature of greater than about 26° C.

4. The temperature change composition of claim 1 wherein the crystalline initiator is selected from fatty alcohols, fatty acids, esters, sugars, salts, crystalline and microcrystalline waxes, microcrystalline triglycerides and combinations thereof.

5. The temperature change composition of claim 1 wherein the carrier is selected from water, glycerin, diglycerin, glycerin derivatives, glycols, glycol derivatives, sugars, ethoxylated and/or propoxylated esters and ethers, urea, sodium PCA, alcohols, ethanol, isopropyl alcohol, and combinations thereof.

6. The temperature change composition of claim 1 wherein the phase change material is selected from a hydrocarbon, a wax, an oil, a natural butter, a fatty acid, a fatty acid ester, a dibasic acid, a dibasic ester, a 1-halide, a primary alcohol, an aromatic compound, an anhydride, an ethylene carbonate, a polyhydric alcohol, and combinations thereof.

7. The temperature change composition of claim 1 wherein the phase change material is selected from tricaprin, parrafin, nonadecane, octadecane, stearyl heptanoate, lauryl lactate, lauryl alcohol, capric acid, caprylic acid, cetyl babassuate, *mangifera indica* (mango) seed butter, *theobroma cacao* (cocoa) seed butter, *butyrospermum parkii* butter, Di-$C_{12-15}$ Alkyl Fumarate, stearyl caprylate, cetyl lactate, cetyl acetate, $C_{24-28}$ alkyl methicone, glyceryl dilaurate, stearamidopropyl PG-dimonium chloride phosphate, jojoba esters, and combinations thereof.

8. The temperature change composition of claim 1 wherein the surfactant is selected from sugar esters and their derivatives, sucrose esters, polyglyceryl esters, sorbitan esters, fatty acid esters, alkylpolyglucosides, and combinations thereof.

* * * * *